United States Patent

Sato et al.

[11] Patent Number: 5,244,918
[45] Date of Patent: Sep. 14, 1993

[54] BENZOFURAN DERIVATIVE AND PHARMACEUTICAL COMPRISING THE SAME AS ACTIVE INGREDIENT

[75] Inventors: Yoshio Sato, Odawara; Naoki Taketomo, Akishima; Yoshihiro Yoshiyama, Okawara; Katsumi Ajisaka, Kanagawa; Itsuro Yokota, Odawara, all of Japan

[73] Assignee: Meiji Milk Products Co., Ltd., Tokyo, Japan

[21] Appl. No.: 720,829

[22] PCT Filed: Nov. 16, 1990

[86] PCT No.: PCT/JP90/01498
§ 371 Date: Jul. 16, 1991
§ 102(e) Date: Jul. 16, 1991

[87] PCT Pub. No.: WO91/07396
PCT Pub. Date: May 30, 1991

[30] Foreign Application Priority Data

Nov. 17, 1989 [JP] Japan .................. 1-300568

[51] Int. Cl.$^5$ .................. A61K 31/34; C07D 307/86
[52] U.S. Cl. ............................ 514/469; 549/462
[58] Field of Search ............. 549/462; 514/469

[56] References Cited

U.S. PATENT DOCUMENTS 4,978,761 12/1991 Goto et al. ............... 549/462

FOREIGN PATENT DOCUMENTS 1-1213276 8/1989 Japan .
2-076870 3/1990 Japan .

OTHER PUBLICATIONS

Ayer et al., Can. J. Microbiol., vol. 36(2), pp. 83–85 (1990).
Pfefferle et al., Journal of Antibiotics, vol. XLIII (6), pp. 648–654 (Jun. 1990).

Primary Examiner—Bernard Dentz
Attorney, Agent, or Firm—Oblon, Spivak, McClelland, Maier & Neustadt

[57] ABSTRACT

The present invention relates to a benzofuran derivative having the following general formula (I),

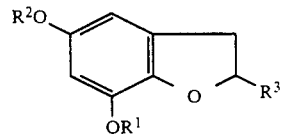

wherein $R^1$ and $R^2$ may be the same or different and represent a hydrogen atom or a lower alkyl group and $R^3$ represents a group —CH=CH—CH=CH—CH$_3$ or a group —(CH$_2$)$_4$CH$_3$, a process for the preparation of the same, an anti-inflammation and anti-allergic agent comprising the same as an effective component, and a novel microorganism producing the compound.

9 Claims, 9 Drawing Sheets

BENZOFURAN DERIVATIVE AND PHARMACEUTICAL COMPRISING THE SAME AS ACTIVE INGREDIENT

FIELD OF THE INVENTION

The present invention relates to benzofuran derivatives possessing inhibitory activity against 5-lipoxygenase which is one of the lipoxygenase metabolic enzymes involving the arachidonate cascade, and, because of this activity, useful for the treatment and prevention of allergic diseases such as bronchial asthma and various inflammatory diseases. The present invention also relates to a process for the preparation of the benzofuran derivatives and a pharmaceutical composition comprising the same.

BACKGROUND ART

A number of factors such as histamine, serotonin, prostaglandin (PG), leukotriene (LT), thromboxane (TX), platelet activation factors, lysolecithin, various types of lymphokine, and the like are involved in the allergic diseases such as bronchial asthma and various inflammatory diseases. Among these factors, PG and LT play particularly important functions in the allergic diseases such as bronchial asthma and various inflammatory diseases because of a number of their analogs and the varieties in their physiological activities. Disorders in the arachidonate metabolic system induces insufficiency or excess in the arachidonate metabolic products such as PG, LT, and TX in the cells, which, in turn, causes many types of pathological conditions, such as vascular permeability progress, bronchial contraction, platelet agglomeration, and the like, leading to various inflammatory diseases and allergic diseases. A number of chemicals which specifically inhibit various enzymes involving the arachidonate metabolic system have been developed as anti-inflammatory drugs; for example, non-steroidal anti-inflammatory drugs, e.g. aspirin and indomethacin, which exhibit anti-inflammatory activity by inhibiting cyclooxygenase activity thereby controlling the production of PG. These drugs are effective for inflammation related to the PG system, but cannot inhibit inflammation induced by LTs. Slow reacting substance of anaphylaxis (SRS-A) is known as a strong chemical mediator of bronchial asthma. SRS-A is a mixture of $CTC_4$, $LTD_4$, and $LTE_4$. $LTB_4$ has strong leukocyte inducing and activating activities, and thus a great attention is given to its involvement in inflammation. Therefore, compounds inhibiting 5-lipoxygenase activity which is the first enzyme catalyzing the production of LTs from arachidonic acid are anticipated to be effective for the treatment or prevention of allergic diseases such as bronchial asthma and various inflammatory diseases.

There are a number of publications reporting compounds having 5-lipoxygenase inhibitory activity from this aspect. Japanese Patent Laid-open (kokai) No. 213276/1989, for example, describes a benzofuran derivative possessing 5-lipoxygenase inhibitory activity and $TXA_2$ biosynthesis inhibitory activity.

Compounds heretofore reported as having 5-lipoxygenase inhibitory activity are not sufficient in their anti-allergic activity, anti-inflammatory activity, and safety. No such compounds are commercially sold as a drug.

The present inventors have screened a number of metabolic products produced by microorganisms using the 5-lipoxygenase inhibitory activity as an index of screening anti-allergic and anti-inflammatory activities. As a result, the present inventors have found a novel benzofuran derivative produced by a microorganism belonging to genus Codinaea possessed remarkable 5-lipoxygenase inhibitory activity as well as anti-allergic and anti-inflammatory activities, and was useful as a medicine. The finding has led to the completion of the present invention.

DISCLOSURE OF THE INVENTION

The present invention provides a benzofuran derivative having the following general formula (I), (I)

wherein $R_1$ and $R_2$ may be the same or different and represent a hydrogen atom or a lower alkyl group and $R^3$ represents a group $-CH=CH-CH=CH-CH_3$ or a group $-(CH_2)_4CH_3$, a process for the preparation of the benzofuran derivative, a pharmaceutical composition comprising the same, and a microorganism producing the same.

BRIEF DESCRIPTION OF THE DRAWINGS

FIGS. 8-1 and 8-2 graphically illustrate the auricle edema inhibitory activity of Compound 1.

BEST MODE FOR CARRYING OUT THE INVENTION

In general formula (I) representing benzofuran derivatives of the present invention, given as examples of $R^1$ and $R^2$ which represent lower alkyl groups are alkyl groups having 1-3 carbon atoms, specifically methyl, ethyl, and n-propyl groups. When $R^3$ in general formula (I) is the group $-CH=CH-CH=CH-CH_3$, there can be four geometrical isomers on account of the two double bonds and optical isomers on account of the asymmetric carbon atom. The present invention includes all these isomers.

Among the compounds of the present invention, 2-(1,3-pentadienyl)-2,3-dihydro-5,7-dihydroxybenzofuran (in general formula (I), $R^1=R^2=H$ and $R^3=-CH=CH-CH=CH-CH_3$; hereinafter referred to as Compound 1) can be prepared, for example, by culturing a microorganism belonging to genus Codinaea and capable of producing Compound 1 and collecting Compound 1, from the culture broth.

An example of microorganisms capable of producing Compound 1 is Codinaea sp. MM-167 (deposited in Fermentation Research Institute, Agency of Industrial Science and Technology as FERM P-11088; hereinafter referred to as MM-167 strain).

Mycological characteristics of MM-167 strain is as follows.

(1) Growth and Morphology in Various Media (i) Malt extract agar medium

Cells grow well and form white aerial hypha, while producing a light brown substance on the back of the medium.

(ii) Potato dextrose agar medium

The growth of the cells is not so well.

(iii) Oatmeal agar medium

The growth of the cells is not so well.

(iv) Miura medium or Ebios medium

Forms conidiums on the end of the aerial hypha.

Figure 1:
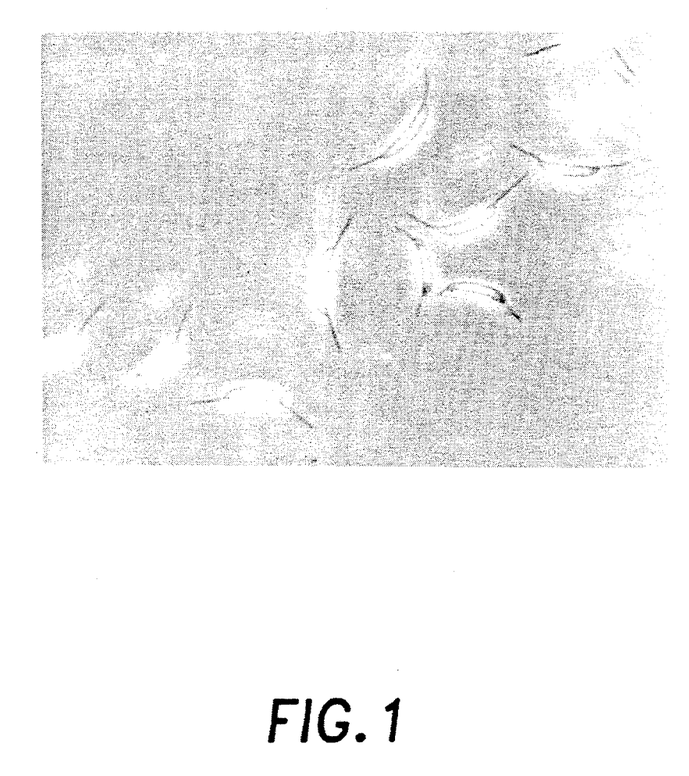
FIG. 1 is a photograph showing the morphology of the conidiums formed on the end of the aerial hypha when Codinaea sp. MM-167 was grown in the Miura medium.

The conidiums are semicircle in shape, 12–16×3–4 μm large, and have vellus, 4–10 μm in length, at both ends. A photograph showing the morphology of the conidiums is given in FIG. 1.

(2) Growth Temperature

Cells grow at about 15°–32° C. The growth is most proliferating in the neighborhood of 25° C.

The MM-167 was identified to be a microorganism belonging to genus Codinaea based on the above characteristics.

Like other strains of microorganisms the characteristics of MM-167 are apt to change. Its mutants can easily be created by an artificial mutagenesis means using UV ray, X ray, various chemicals, and the like. The mutants thus obtained can be used in the present invention inasmuch as they can produce Compound 1.

In order to prepare Compound 1, the above strain is aerobically cultured in a medium containing nutrients with which normal microorganisms can grow. Known nutritious sources used in the culture of conventional microorganisms can be used. As a medium, a medium known as the malt extract medium which is comprised of malt extract, peptone, and glucose, or a liquid medium such as C4 medium can be preferably used. Various aerobic cultivation methods known in the art can be used for the culture. The most preferable method from the aspect of mass production is the shake culture in a liquid medium. A preferable cultivation temperature is about 15°–30° C. and a pH in a neutral or weak alkaline range is preferred for the medium. Compound 1 is accumulated in 3–5 days after start of the cultivation. The cultivation is then terminated, and the culture broth is filtered to collect the supernatant. For collecting Compound 1 from the supernatant thus obtained, the supernatant is submitted to adsorption column chromatography and eluted with methanol. Fractions exhibiting 5-lipoxygenase inhibitory activity is concentrated and submitted to silica gel column chromatography to elute with a n-hexane solvent containing 25–30% of ethyl acetate. The eluate is concentrated under reduced pressure to produce white powder, which is then recrystallized from a water-ethanol solvent to obtain Compound 1 as a plate-like white substance.

Of the compounds of the present invention, compounds having group —$(CH_2)_4CH_3$ for $R_3$ can be prepared, for example, according to the following reaction.

In the above reaction formula, $R^1$ and $R^2$ have the same meanings as defined above.

Specifically, a compound of formula (III) can be obtained by catalytically hydrogenating a compound of formula (II). The hydrogenation is preferably carried out by using hydrogen gas occluded in palladium-activated carbon.

Of the compounds of the present invention, compounds having a lower alkyl group for $R^1$ and/or $R^2$ can be prepared, for example, according to the following reaction.

In the above reaction formula, at least one of $R^4$ and $R^5$ is a lower alkyl group and $R^3$ have the same meaning as defined above.

Specifically, a compound of formula (V) can be obtained by the alkylation of a compound of formula (IV). The common O-alkylation reaction can be employed for the alkylation reaction by using diazomethane, halogenated alkyl, alkyl sulfate, or the like as an alkylation agent.

The compounds of the present invention exhibit remarkable 5-lipoxygenase inhibitory activity (e.g. Compound 1 shows 50% inhibition at the concentration ($IC_{50}$ value) of $2.0\times10^{-6}M$) in the arachidonate cascade, and inhibit the production of 5(S)-hydroperoxyeicosatetraenoic acid (5-HPETE), leukotriene, 5(S)-hydroxyeicosatetraenoic acid (5-HETE), and the like which are the metabolic products of 5-lipoxygenase. The compounds of the present invention significantly inhibit arachidonic acid-derived edema in paws of rats by oral administration, and dose-dependently inhibit arachidonic acid-derived auricle edema in rats. Furthermore, they concentration-dependently inhibit SRS-A production by the anaphylaxis reaction from a portion of lung cut from a guinea pig. These experimental results and extremely low toxicity shown in toxicity tests demonstrate that a drug comprising a compound of the present invention is useful for the treatment and prevention of allergic diseases such as bronchial asthma; rheumatism; and various inflammatory diseases such as psoriasis and the like.

A pharmaceutical composition comprising a compound of the present invention can be orally or non-orally administered as is or after formed into tablets, capsules, liquid preparations, injections, suppositories, or the like by using conventional carriers and vehicles. Although a dose is dependednt on the subject, the manner of administration, the symptoms, and the like, a dose for bronchial asthma in adult, for example, may be 0.1–50 mg/kg of body weight.

EXAMPLES

The present invention is hereinafter described by way of examples, which shall not be construed as limiting the present invention.

EXAMPLE 1 (Preparation of Compound 1)

<Cultivation>

| Medium Composition (C4 Medium) | |
|---|---|
| Bacto-soytone (Difco) | 2.5 g |
| Glucose | 2.0 |
| Soluble starch | 1.0 |
| (Wako Pure Chemicals Co., Ltd.) | |
| Yeast extract (Difco) | 0.4 |
| Meat extract | 0.1 |
| (Kyokuto Pharmaceutical Co., Ltd.) | |
| NaCl | 0.2 |
| $K_2HPO_4$ | 0.005 |
| Purified water | 100 ml |
| pH | 7.3 |

The C4 medium of the above composition (100 ml) was dispensed into a 500 ml conical flask and sterilized at 121° C. for 20 minutes in an autoclave. MM-167 strain was inoculated with a platinum loop into the sterilized medium and shake-cultured at 25° C. and 250 rpm for 3 days to produce a seed culture broth.

For the production of Compound 1, 1 l of fresh C4 medium was charged into a 3 l conical flask and sterilized at 121° C. for 20 minutes in an autoclave to obtain a production medium. 20 ml of the above seed culture broth was inoculated into the production medium for cultivation at 25° C. and 250 rpm for 3 days. The culture broth thus obtained was submitted to a suction filter to separate a supernatant from the microorganism cells.

<Purification>

The supernatant was charged into an adsorption chromatography column HP-20 (length: 35 cm, diameter: 60 mm, made by Nippon Rensui Co., Ltd.) and eluted with water, 10% methanol, 50% methanol, and then 100% methanol. Of the fractions thus obtained, only those eluted with 100% methanol were confirmed to exhibit 5-lipoxygenase inhibitory activity. The fractions exhibiting 5-lipoxygenase inhibitory activity were concentrated to dryness under reduced pressure, charged into a silica gel column (length: 40 cm, diameter: 60 mm, 100–200 mesh, made by Kanto Chemical Co., Ltd.), and eluted with n-hexane-ethyl acetate while progressively increasing the concentration of ethyl acetate in the solvent. The 5-lipoxygenase inhibitory activity was confirmed to be exhibited by the fractions eluted with solvent with 25–30% ethyl acetate concentration. The fractions exhibiting 5-lipoxygenase inhibitory activity were concentrated under reduced pressure to obtain white powder. The powder was dissolved into a small amount of ethanol, and to the solution was added water to make the concentration of the powder 10 mg/ml. The solution was allowed to stand overnight to obtain 108 mg of white plate-like crystals of Compound 1.

Melting point: 125°–126° C.
Specific rotation:

$$[\alpha]_D^{20} = -15° \ (C=2.0, \text{ethanol}).$$

Figure 2:
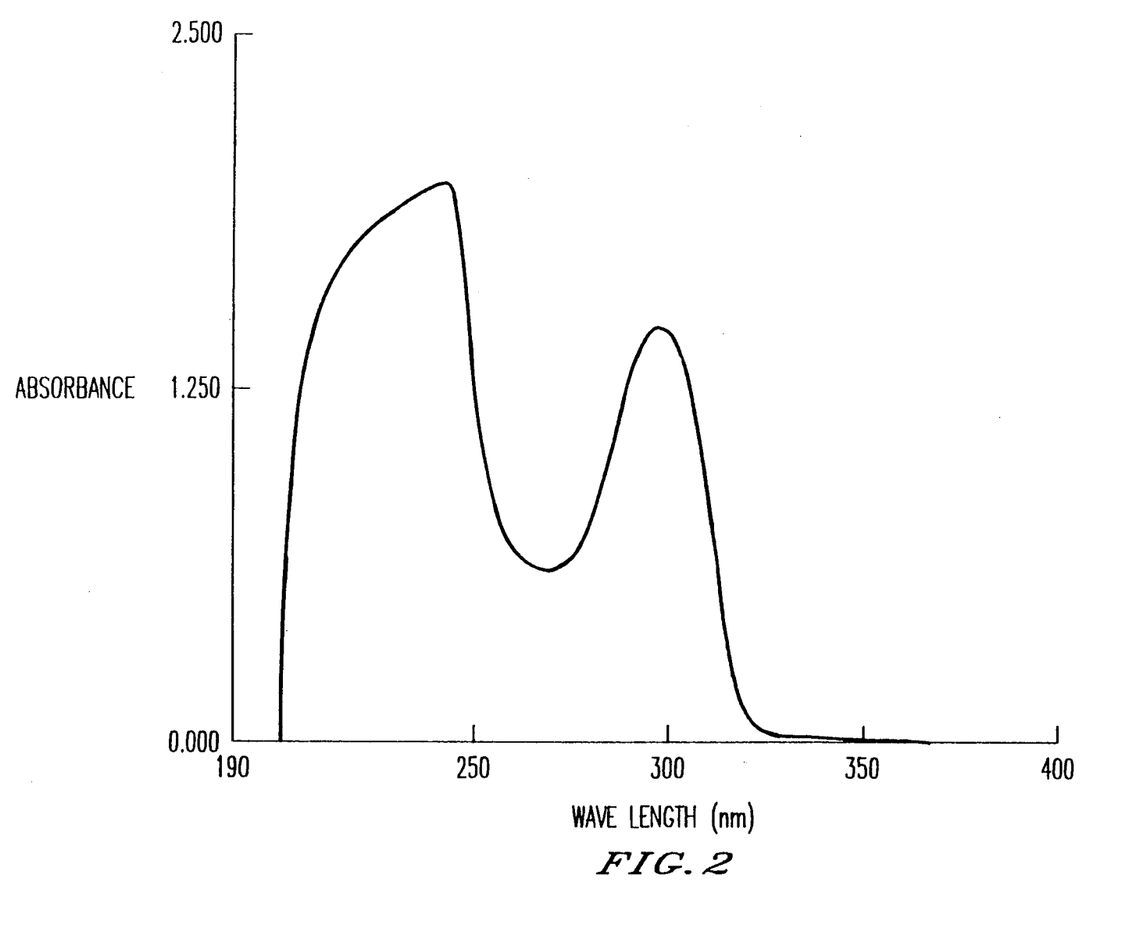
FIG. 2 is a UV spectrum of Compound 1.
Figure 3:
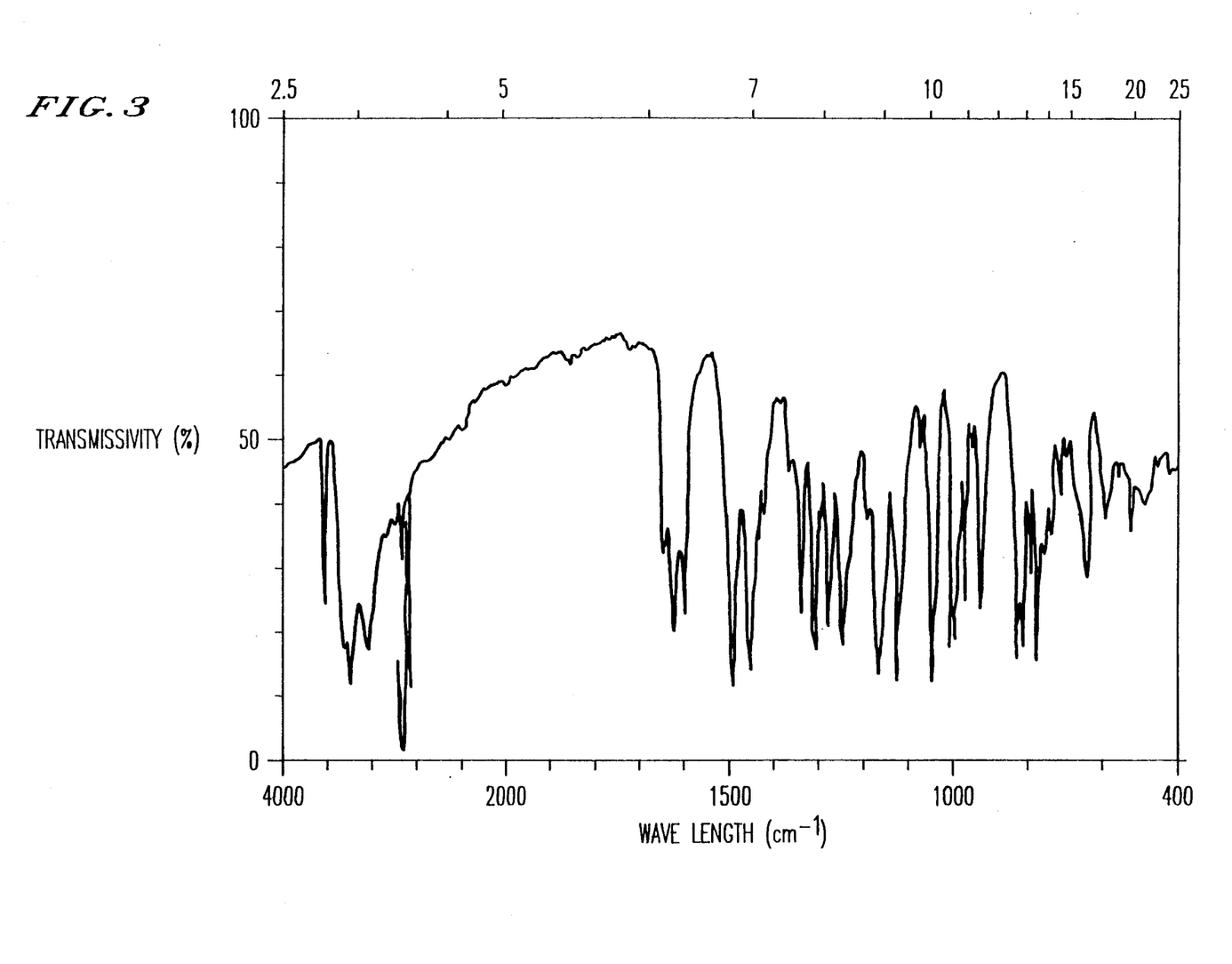
FIG. 3 is an IR spectrum of Compound 1.
Figure 4:
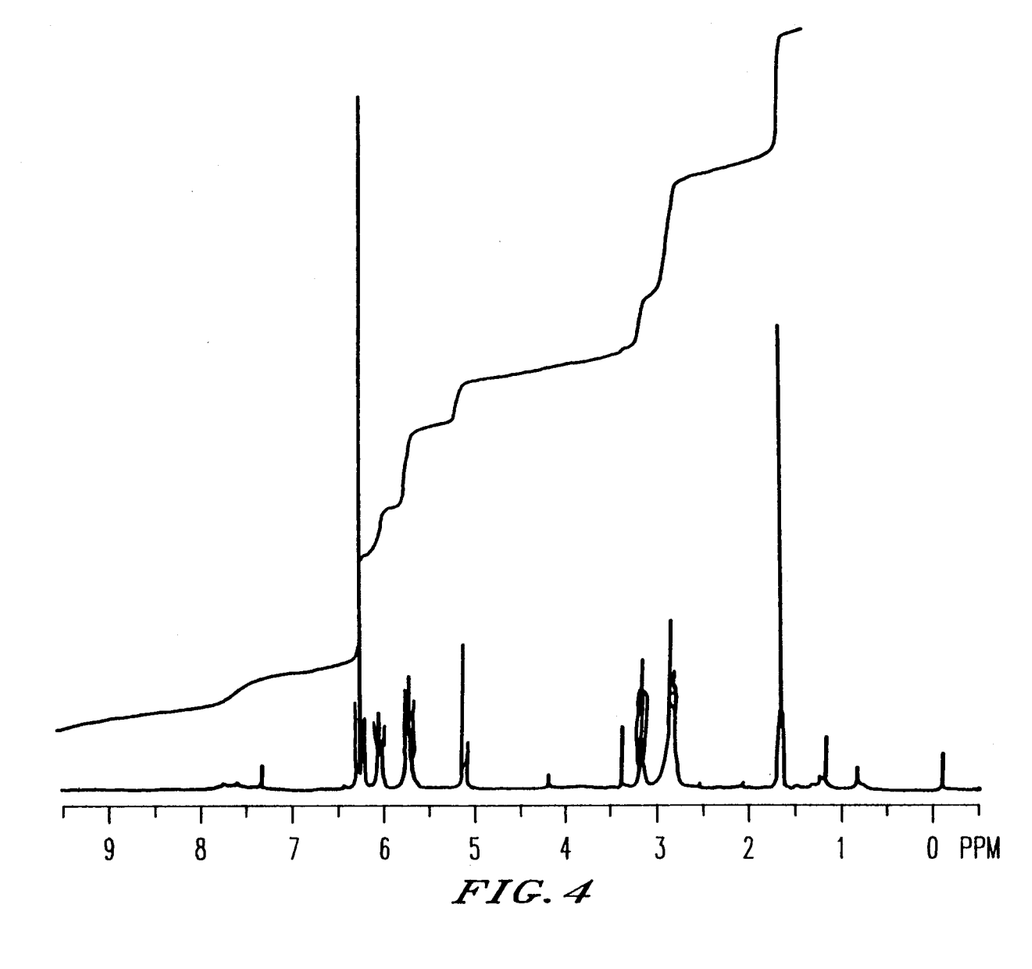
FIG. 4 is an NMR spectrum of Compound 1.

UV Spectrum: given in FIG. 2 (1 mg/ml methanol).
IR Spectrum: given in FIG. 3 (KBr Tablet method).
400 MHz Proton NMR Spectrum: given in FIG. 4. (Solvent: $CDCl_3$, Internal standard: $(CH_3)_4Si$).

Compound 1 can be represented by the name 2-(1-tans, 3-trans-pentadienyl)-2,3-dihydro-5,7-dihydroxybenzofuran.

EXAMPLE 2

Figure 5:
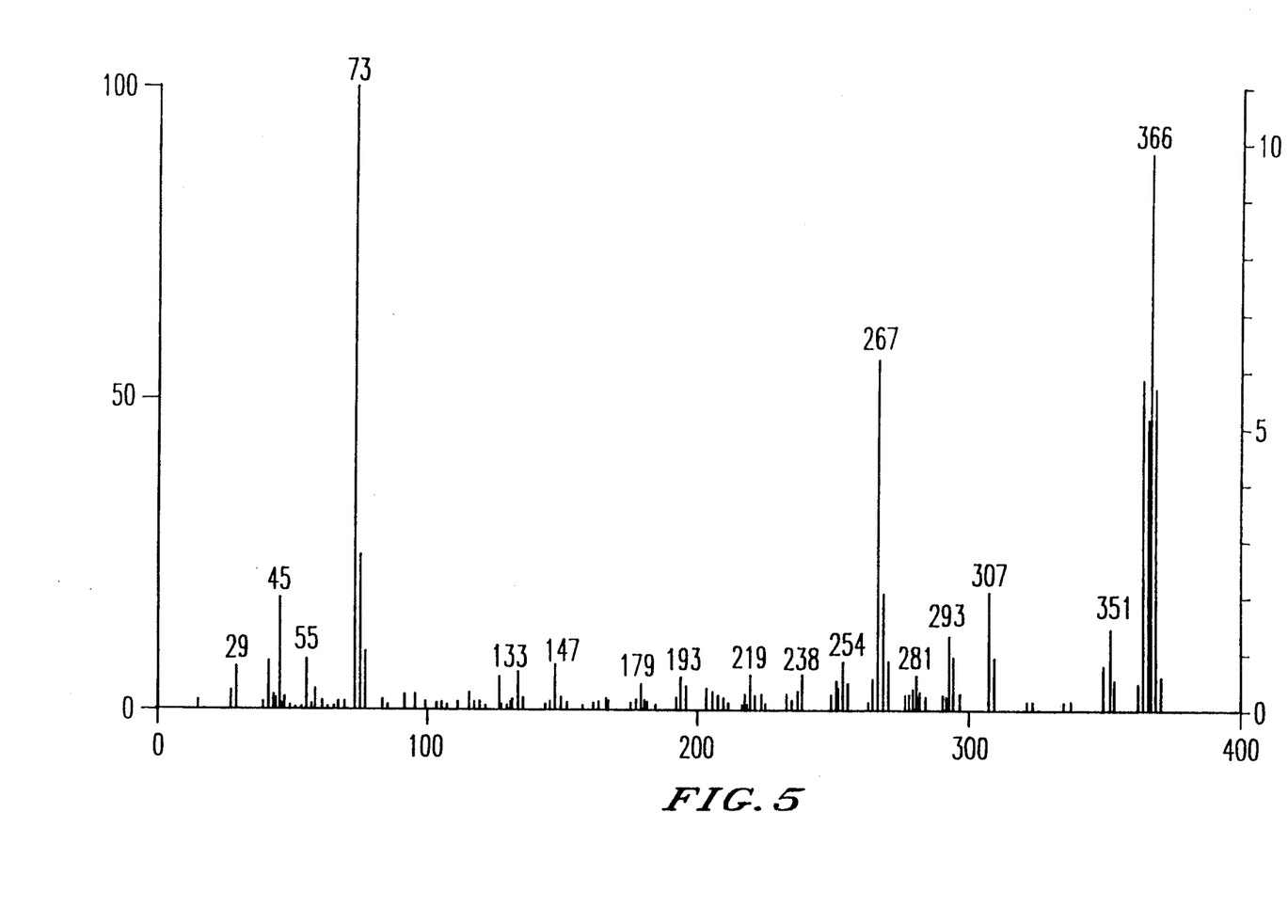
FIG. 5 is a mass spectrum of Compound 2.

Hydrogen gas was injected to saturation into a suspension of 500 mg of palladium-activated carbon in 50 ml of methanol for occlusion of hydrogen gas in palladium-activated carbon. To the suspension was added a solution of 20.2 mg of Compound 1 in 1 ml of methanol, followed by stirring at room temperature for 30 minutes to effect the reaction and to obtain 2-n-pentyl-2,3-dihydro-5,7dihydroxybenzofuran (Compound 2: $R^1=R^2=H$, $R^3=-(CH_2)_4CH_3$ in formula (I)). The mass spectrum of Compound 2 is given in FIG. 5.

EXAMPLE 3

Figure 6:
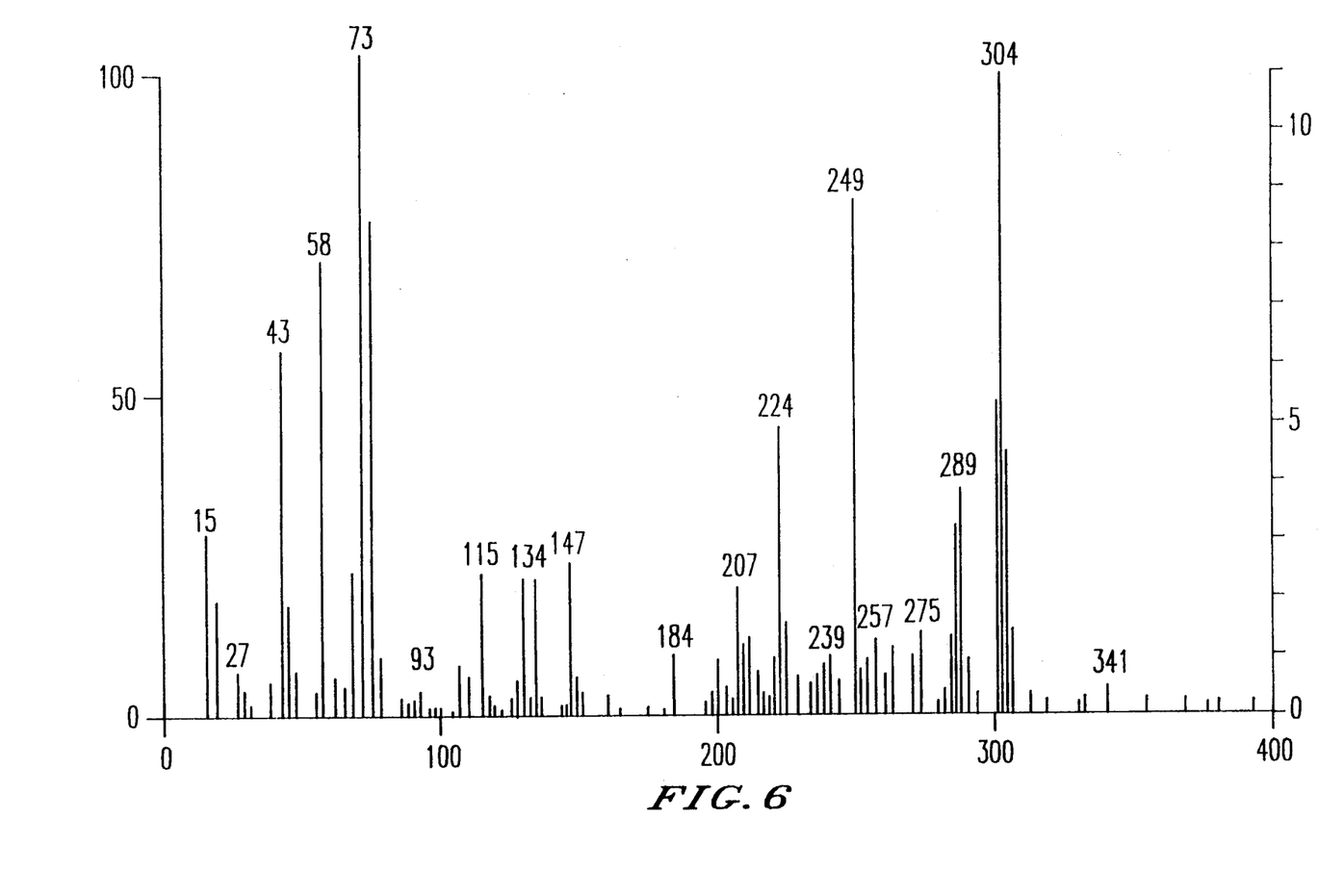
FIG. 6 is a mass spectrum of Compound 3.

To a solution of 20.2 mg of Compound 1 in 10 ml of methanol was added diazomethane dissolved in ether, and the mixture was stirred at room temperature for 12 hours to effect the reaction and to obtain 2-(1,3-pentadienyl)-2,3-dihydro-5-hydroxy(or methoxy)-7-methoxy(or hydroxy)benzofuran (Compound 3: $R^1=H$ (or $CH_3$), $R^2=CH_3$ (or H), $R^3=-CH=CH-CH=CHCH_3$ in formula (I)). The mass spectrum of Compound 3 is given in FIG. 6.

EXAMPLE 4

Figure 7:
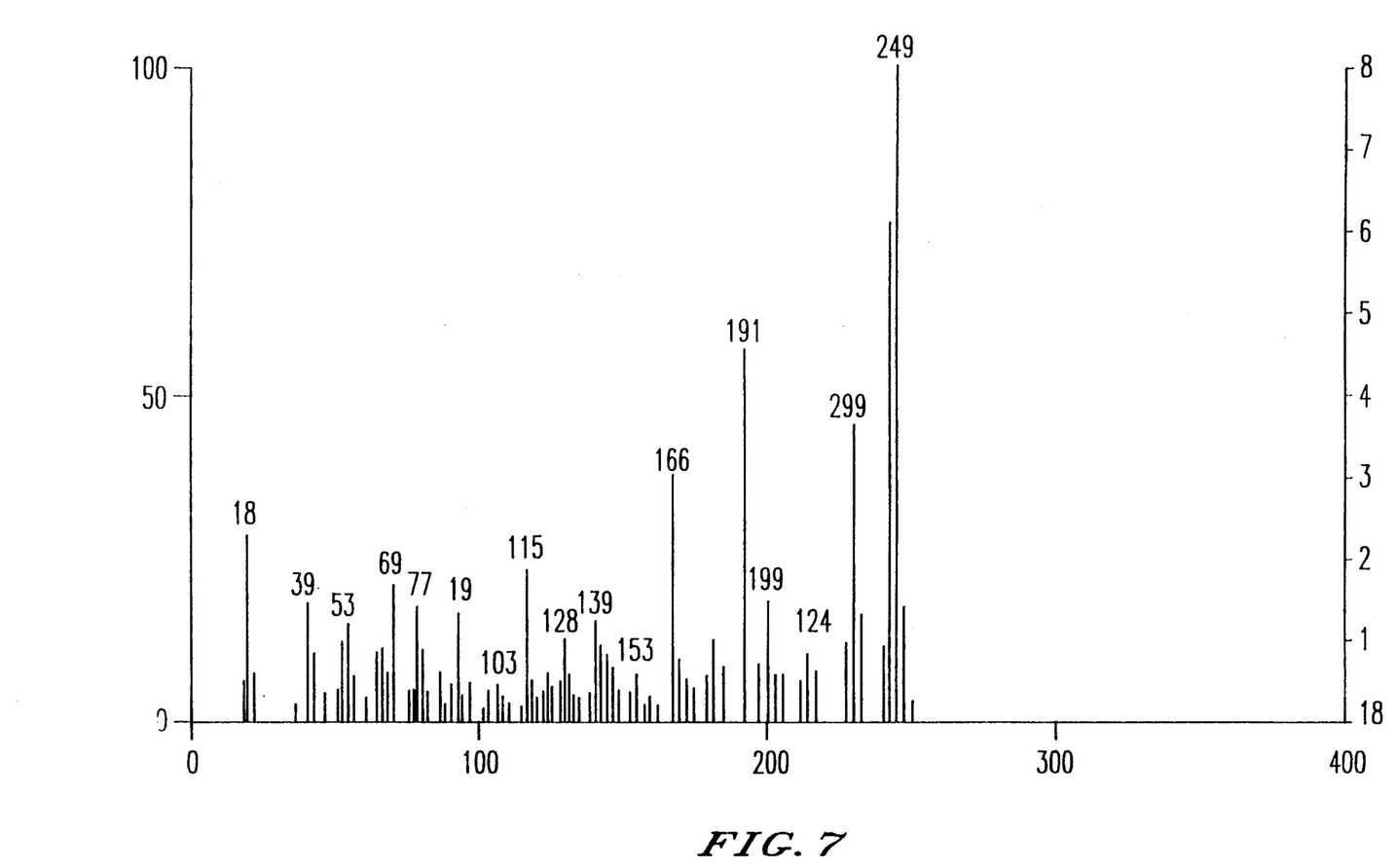
FIG. 7 is a mass spectrum of Compound 4.

To a solution of 20.2 mg of Compound 1 in 50 ml of acetone were added 3 g of $CH_3I$ and 60 mg of $K_2CO_3$. The mixture was refluxed at 90° C. for 5 hours to obtain 2-(1,3-pentadienyl)-2,3-dihydro-5,7-dimethoxybenzofuran (Compound 4: $R^1=R^2=CH_3$, $R^3=-CH=CH-CH=CHCH_3$ in formula (I)) The mass spectrum of Compound 4 is given in FIG. 7.

Test Example 1 (5-Lipoxygenase Inhibitive Activity)

$2.5 \times 10^7$ RBL-1 cells (rat basophilic leukemia cells, purchased from Dainippon Pharmaceutical Co. Ltd.) were washed twice with 0.1M Tris-HCl buffer (pH 7.5) and ultrasonicated. The pulverized cell liquid was subjected to ultracentrifugation at $100,000 \times g$ for 90 minutes to collect a supernatant, which was served as a 5-lipoxygenase enzyme liquid in the test. 250 μl of the enzyme liquid was reacted with a reaction liquid consisting of 1.75 ml of 0.1M Tris-HCl buffer (pH 7.5), 100 μM arachidonic acid, 1 ml of $CaCl_2$, 1 mM ATP (adenosine triphosphate), and a compound of the present invention (with ultimate concentrations of 10 μM, 3.0 μM, 1.0 μM, 0.3 μM, and 0.1 μM) at 37° C. for 10 minutes. After terminating the reaction by an addition of 50 μl of 1N HCl, the reaction mixture was extracted with 6 ml of ethyl acetate. The extract was concentrated under reduced pressure and the concentrate was submitted to HPLC according to the method of Amano et al. [Vitamin, 59, 211-219 (1985)] to quantitatively determine the amount of 5-HETE by an UV analyzer. The concentration of the compound of the present invention inhibiting 50% of 5-lipoxygenase ($IC_{50}$) is expressed by the concentration of the compound of the present invention inhibiting the production of 5-HETE as much as 50% as compared with the controls. The results are shown in Table 1, which demonstrates that compounds of the present invention possess 5-lipoxygenase inhibitory activity. Compound 1 possesses a specific 5-lipoxygenase inhibitory activity.

TABLE 1

| Tested Compound | $IC_{50}$ (M) |
| --- | --- |
| Compound 1 | $2.0 \times 10^{-6}$ |
| Compound 2 | $1.2 \times 10^{-6}$ |
| Compound 3 | $1.5 \times 10^{-6}$ |

Test Example 2 (Edema Inhibitive Activity)

2-1 Edema Inhibitive Activity in Rat Soles

In vivo anti-inflammatory action of Compound 1 was tested using edema in paws of rats as a model.

Wister male rats (Japan Charles River), weighing 150-170 g, 6 week age, were fasted from the previous day of the test for serving to the experiment.

Samples (10 ml/kg) were orally administered to the control (solvent: 0.5% gum arabica) group and Compound 1 (200 mg/kg body weight) test group. After 2 hours, 100 µl of a sodium arachidonate solution (5 mg/ml, 0.1M carbonate buffer, pH 8.4) was injected in the paw to determine the increase of the edema volume after 1 hour. The increase of the edema volume was determined by subtracting the value measured 1 hour before the administration of arachidonate from the value measured 1 hour after the administration. The foot volume increase (ml, means±S.D.) in the control group was 0.822±0.131 (n=10), whereas that in Compound 1 test group was 0.664±0.104 (n=8). Thus, the edema inhibitory effect of Compound 1 test group was confirmed to be 19.2% higher than that in the control group. Since the above two groups exhibited homogeneous variances (the F-test by Snedector, $p<0.05$), the T-test by Student was carried out, confirming a statistical significance ($p<0.05$).

2-2 Auricle Edema Inhibitive Activity in Mice

In vivo anti-inflammatory action of Compound 1 was tested using auricle edema in mice as a model.

ICR male mice (Japan Charles River), weighing 29.9-40.4 g, 8 week age, were anesthetized with pentobarbital (Trademark: Nembutal, manufactured by Dainabott-Dainippon Pharmaceutical Co., Ltd.) to measure the thickness of the right ear with a dial thickness gauge. 20 µl of Compound 1 and control compound (acetone) were applied (the amount hereinafter specified) to the inside of the right ear with microsyringe, and, 30 minutes later, 2 mg of arachidonic acid was applied in the same manner to the inside of the right ear. The thickness of the right ear was measured 60 minutes after the application of arachidonic acid. Mice were then sacrificed by vertebral cervical dislocation and a circle with a diameter of 7 mm was cut out from the center of the right ear with an ear punch to measure its weight. The test was performed twice; the amounts of Compound 1 applied were 4 mg, 1 mg, 0.4 mg, 0.04 mg, and 0.004 mg per ear for the first test and 1 mg, 0.2 mg, 0.04 mg, 0.008 mg, and 0.0016 mg per ear for the second test. Both Compound 1 and arachidonic acid were used as dissolved in acetone.

Figure 81:
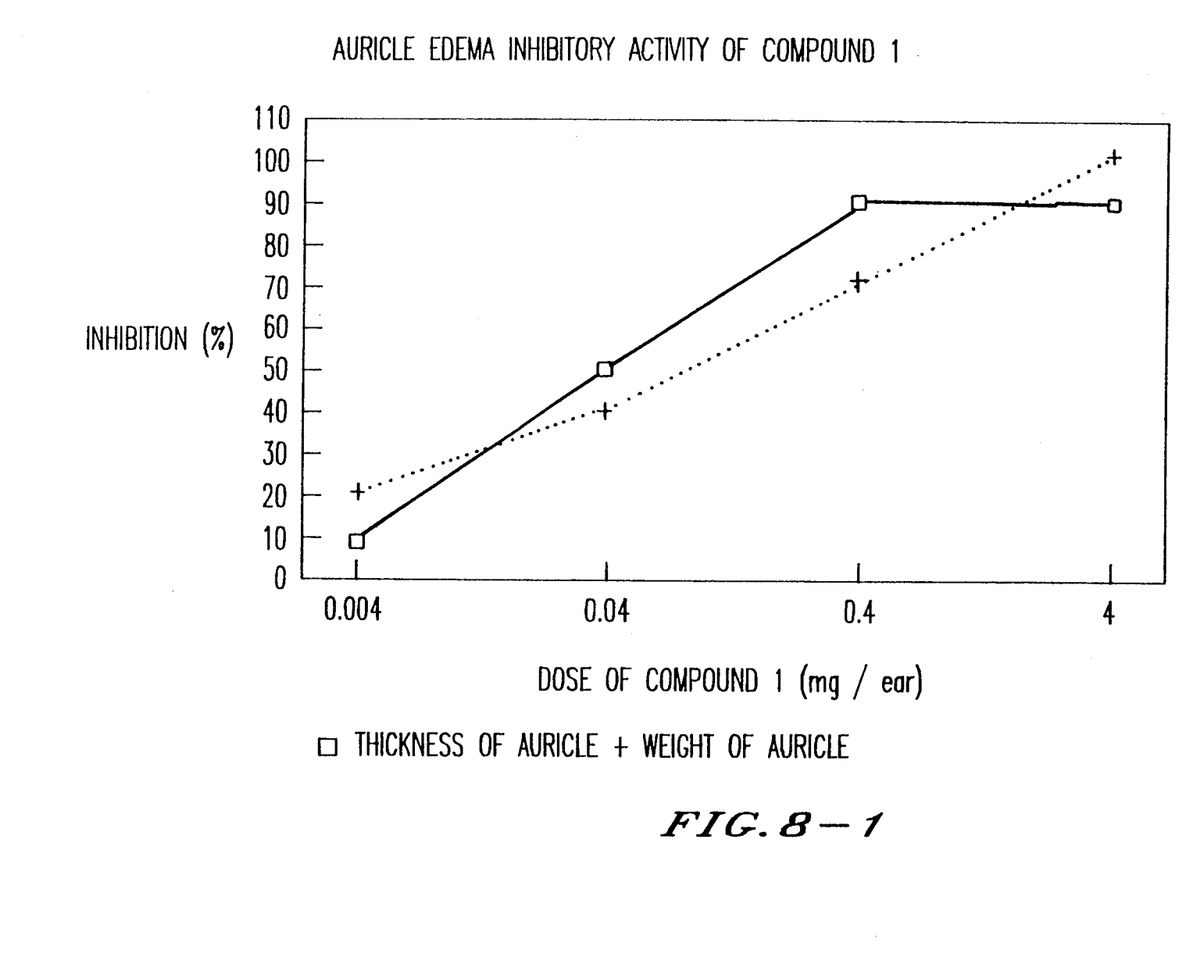
Figure 82:
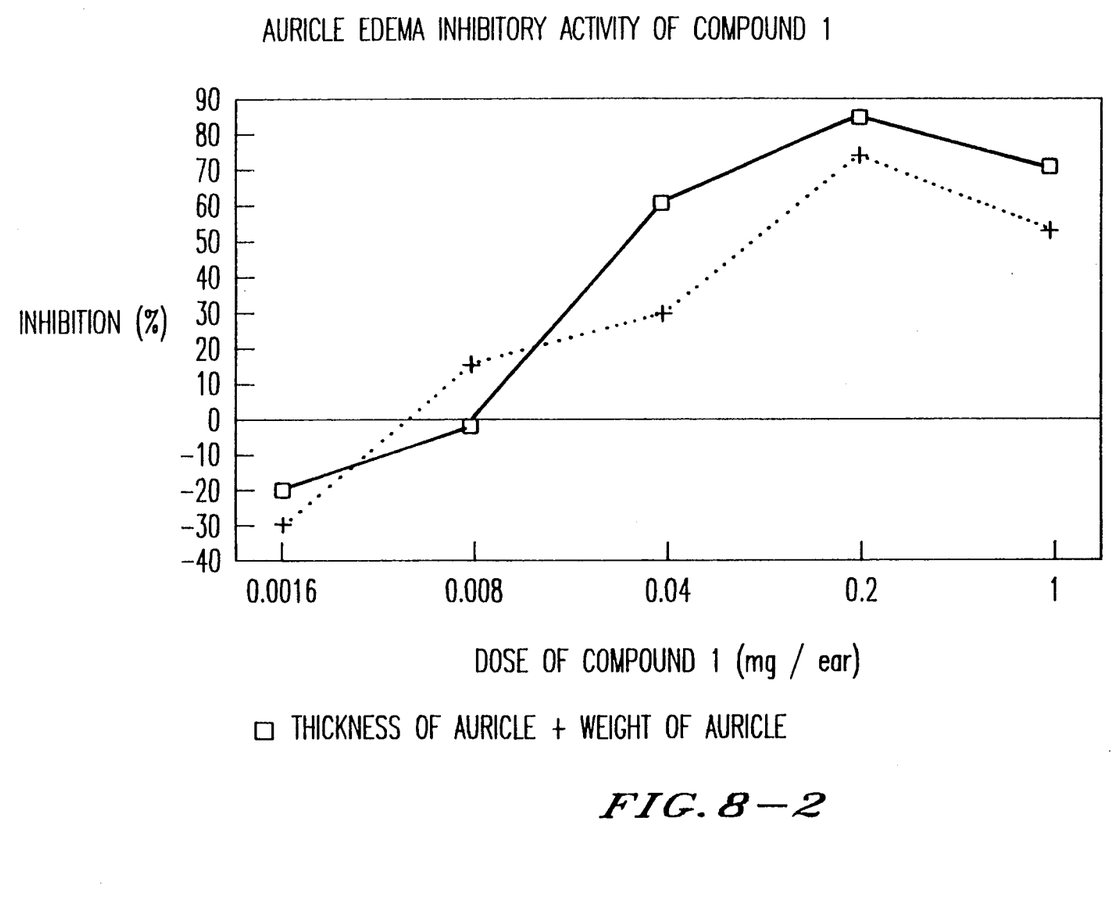

The results are shown in FIG. 8-1 (the first test) and FIG. 8-2 (the second test). In the second test, the thickness of the ear and its weight showed almost the same results, demonstrating a dose dependent inhibitory effect of Compound 1 against the auricle edema induced with arachidonic acid. The 50% effective dose ($ED_{50}$) in the two experiments were very close to each other, 0.03-0.08 mg/ear.

Test Example 3 (SRS-A Production Inhibitive Activity)

$LTC_4$ and $LTD_4$ which consist of SRS-A are very strong chemical mediators of allergic bronchial asthma and the like. The inhibitory effect of Compound 1 against the production of SRS-A was therefore biologically measured.

A suspension of 1 mg of egg white albumin and 0.5 ml of complete Freund's adjuvant was intraperitoneally injected to Hartley male guinea pigs. The same antigen liquid was again injected 2 or 3 weeks thereafter to effect the sensitization. The sensitized guinea pigs were sacrificed by bleeding, and the lung was washed with a Tyrode's solution and cut into pieces to prepare lung fragment specimens. 300 mg of the lung fragments were floated on 2.8 ml of the Tyrode's solution. After shaking the solution at 37° C. for 20 minutes, 0.1 ml of Compound 1 was added. Shaking this solution was carried out for a further 5 minutes, followed by the addition of 0.1 ml of an egg white albumin solution (the ultimate antigen concentration: 1 mg/ml). After the reaction at 37° C. for 20 minutes, 12 ml of methanol was added and the mixture was stirred. The reaction mixture was centrifuged, the supernatant was concentrated under reduced pressure to dryness, and the dry solid was dissolved into 1 ml of water to biologically measure LTs (SRS-A) contained therein.

The determination of the quantity of SRS-A produced was carried out by using the ileum enucleated from Hartley male guinea pigs and counting the constriction of the ileum in the presence of $10^{-6}$M Atropine and Pyrilamine. A standard curve for the standard sample was prepared based on $LTD_4$ to determine the amount of SRS-A produced by the effect of Compound 1 as the amount of $LTD_4$. As a result, the SRS-A production inhibitory effect of Compound 1 was found to be dependent on the concentration and the 50% inhibition concentration was found to be $4.0 \times 10^{-6}$M. The effect was considered to be equivalent to a known 5-lipoxygenase inhibitory agent, AA-861, having the 50% inhibition concentration of $1.8 \times 10^{-6}$M [Prostaglandins 26, 955-973 (1983)].

Test Example 4 (Single Administration Toxicity Test in Mice)

Compound 1 was intravenously or intraperitoneally administered one time to groups of ICR male mice (age: 5 weeks, purchased from Japan SLC Co.), each group consisting of 5, to observe the death of the mice in 14 days. In the case of intravenous administration, no mice were dead at a technically allowable maximum dose, 20 mg/kg. No abnormality was observed in the general conditions and the body weight, and in the results of autopsy. Thus, the fatal dose of Compound 1 in single intravenous administration to mice was above 20 mg/kg. In the case of intraperitoneal administration, no death in the mice occurred at a dose of 25 mg/kg, 50 mg/kg, and 100 mg/kg. A temporary slight decrease in the body weight was observed at a dose of 50 mg/kg and 100 mg/kg, but the weight change thereafter was normal. No abnormality was observed in the general conditions and in the results of autopsy. The fatal dose of Compound 1 in single intraperitoneal administration to mice was about 100 mg/kg or more.

Industrial Application

The compounds of the present invention possess remarkable 5-lipoxygenase inhibitory activity and excellent anti-allergic and anti-inflammatory effects. They are useful as a medicine for the treatment and prevention of allergic diseases such as bronchial asthma; rheumatism; and various inflammatory diseases such as psoriasis and the like.

What is claimed is:

1. A substantially pure benzofuran derivative having the following formula (I), wherein $R^1$ and $R^2$ may be the same or different and represent a hydrogen atom on a lower alkyl group and $R^3$ represents a group —CH=CH—CH=CH—CH$_3$ or a group —(CH$_2$)$_4$CH$_3$.

2. An anti-inflammation agent comprising the benzofuran derivative having the following formula wherein $R^1$ and $R^2$ may be the same or different and represent a hydrogen atom or a lower alkyl group and $R^3$ represents a group —CH=CH—CH=CH—CH$_3$ or a group —(CH$_2$)$_4$CH$_3$ as an effective component in an anti-inflammatory effective amount in a conventional pharmaceutically acceptable carrier or vehicle.

3. An anti-allergic agent comprising the benzofuran derivative having the following formula wherein $R^1$ and $R^2$ may be the same or different and represents a hydrogen atom or a lower alkyl group and $R^3$ represents a group —CH=CH—CH=CH—CH$_3$ or a group —(CH$_2$)$_4$CH$_3$ as an effective component in anti-allergically effective amount in a conventional pharmaceutically acceptable carrier or vehicle.

4. The substantially pure compound 2-(1-trans, 3-trans-pentadienyl)-2,3-dihydro-5,7-dihydroxybenzofuran.

5. The compound 2-n-pentyl-2,3-dihydro-5,7-dihydroxybenzofuran.

6. An anti-inflammation agent comprising the compound of claim 4 as an effective component in an anti-inflammatory effective amount in a conventional pharmaceutically acceptable carrier or vehicle.

7. An anti-inflammation agent comprising the compound of claim 5 as an effective component in an anti-inflammatory effective amount in a conventional pharmaceutically acceptable carrier or vehicle.

8. The process of treating a patient having an allergic disease which comprises administering to the patient an anti-allergic effective amount of a compound of the following formula wherein $R^1$ and $R^2$ may be the same or different and represent a hydrogen atom or a lower alkyl group and $R^3$ represents a group —CH=CH—CH=CH—CH$_3$ or a group —(CH$_2$)$_4$CH$_3$.

9. The process of treating a patient having an inflammatory condition which comprises administering to the patient an anti-inflammatory effective amount of a compound of the following formula wherein $R^1$ and $R^2$ may be the same or different and represent a hydrogen atom or a lower alkyl group and $R^3$ represents a group —CH=CH—CH=CH—CH$_3$ or a group —(CH$_2$)$_4$CH$_3$.

* * * * *

UNITED STATES PATENT AND TRADEMARK OFFICE
CERTIFICATE OF CORRECTION

PATENT NO. : 5,244,918
DATED : September 14, 1993
INVENTOR(S) : Yoshio Sato et al.

It is certified that error appears in the above-indentified patent and that said Letters Patent is hereby corrected as shown below:

On the title page, Item [75],

The third inventor's city should read: --Odawara--

Signed and Sealed this

Eighteenth Day of April, 1995

*Attest:*

BRUCE LEHMAN

*Attesting Officer*  *Commissioner of Patents and Trademarks*